US010918363B2

(12) United States Patent
Godara et al.

(10) Patent No.: US 10,918,363 B2
(45) Date of Patent: *Feb. 16, 2021

(54) SYSTEMS AND METHODS FOR TRACK COAGULATION

(71) Applicant: Medtronic Holding Company Sàrl, Tolochenaz (CH)

(72) Inventors: Neil Godara, Milton (CA); Jason Woo, Mississauga (CA)

(73) Assignee: MEDTRONIC HOLDING COMPANY SÄRL, Tolochenaz (CH)

( * ) Notice: Subject to any disclaimer, the term of this patent is extended or adjusted under 35 U.S.C. 154(b) by 344 days.

This patent is subject to a terminal disclaimer.

(21) Appl. No.: 15/879,572

(22) Filed: Jan. 25, 2018

(65) Prior Publication Data

US 2018/0146957 A1 May 31, 2018

Related U.S. Application Data

(63) Continuation of application No. 14/195,972, filed on Mar. 4, 2014, now Pat. No. 9,877,707.
(Continued)

(51) Int. Cl.
*A61B 18/14* (2006.01)
*A61B 10/02* (2006.01)
(Continued)

(52) U.S. Cl.
CPC ........ *A61B 10/025* (2013.01); *A61B 18/1477* (2013.01); *A61B 2018/00005* (2013.01);
(Continued)

(58) Field of Classification Search
CPC .............. A61B 10/025; A61B 18/1477; A61B 2018/00005; A61B 2018/00023; A61B 2018/00565; A61B 2018/00589; A61B 2018/00642; A61B 2018/00702; A61B 2018/00714; A61B 2018/0072;
(Continued)

(56) References Cited

U.S. PATENT DOCUMENTS 5,417,713 A * 5/1995 Cohen ..................... A61N 1/39
607/124
5,607,389 A 3/1997 Edwards et al.
(Continued)

OTHER PUBLICATIONS

Groenemeyer, Dietrich H.W. et al. Image-guided Percutaneous Thermal Ablation of Bone Tumours. Academic Radiology, vol. 9, No. 4, Apr. 2002.
(Continued)

*Primary Examiner* — Michael F Peffley
*Assistant Examiner* — Amanda L Zink

(57) ABSTRACT

Devices, and methods of use thereof, are disclosed for preventing tumor seeding when withdrawing the device along an entry-exit path. Some embodiments of the present invention comprise a method of withdrawing a probe through a tissue via a path that traverses at least some bone tissue, the method including withdrawing the probe through the path, and at least partially concurrently delivering energy in a bipolar manner from the probe to heat a layer of tissue surrounding the probe to a temperature sufficient for thermal coagulation necrosis of cells. The device may be withdrawn incrementally.

20 Claims, 11 Drawing Sheets

Related U.S. Application Data

(60) Provisional application No. 61/774,213, filed on Mar. 7, 2013.

(51) Int. Cl.
*A61B 18/00* (2006.01)
*A61B 18/12* (2006.01)

(52) U.S. Cl.
CPC ............ *A61B 2018/00023* (2013.01); *A61B 2018/0072* (2013.01); *A61B 2018/00565* (2013.01); *A61B 2018/00589* (2013.01); *A61B 2018/00642* (2013.01); *A61B 2018/00702* (2013.01); *A61B 2018/00714* (2013.01); *A61B 2018/00755* (2013.01); *A61B 2018/00767* (2013.01); *A61B 2018/00779* (2013.01); *A61B 2018/00791* (2013.01); *A61B 2018/00875* (2013.01); *A61B 2018/00892* (2013.01); *A61B 2018/126* (2013.01); *A61B 2018/1425* (2013.01)

(58) Field of Classification Search
CPC .......... A61B 2018/00755; A61B 2018/00767; A61B 2018/00779; A61B 2018/00791; A61B 2018/00875; A61B 2018/00892; A61B 2018/126; A61B 2018/1425
See application file for complete search history.

(56) References Cited

U.S. PATENT DOCUMENTS

| | | | |
|---|---|---|---|
| 5,935,123 A | 8/1999 | Edwards et al. | |
| 5,947,964 A | 9/1999 | Eggers et al. | |
| 6,106,524 A | 8/2000 | Eggers et al. | |
| 6,261,242 B1 | 7/2001 | Roberts et al. | |
| 6,306,132 B1* | 10/2001 | Moorman | A61B 10/0233 600/562 |
| 6,355,033 B1* | 3/2002 | Moorman | A61B 10/0233 606/33 |
| 6,398,782 B1* | 6/2002 | Pecor | A61B 17/0057 606/46 |
| 6,413,255 B1* | 7/2002 | Stern | A61B 18/14 606/41 |
| 6,592,530 B1 | 7/2003 | Farhadi | |
| 6,770,070 B1 | 8/2004 | Balbierz | |
| 7,160,292 B2 | 1/2007 | Moorman et al. | |
| RE40,388 E * | 6/2008 | Gines | A61B 18/1206 606/34 |
| 2002/0022835 A1* | 2/2002 | Lee | A61B 17/42 606/34 |
| 2003/0093007 A1 | 5/2003 | Wood | |
| 2003/0097079 A1 | 5/2003 | Garcia | |
| 2003/0109802 A1* | 6/2003 | Laeseke | A61B 10/0275 600/564 |
| 2005/0177209 A1* | 8/2005 | Leung | A61B 18/148 607/101 |
| 2009/0118727 A1* | 5/2009 | Pearson | A61B 18/1482 606/41 |
| 2010/0010480 A1* | 1/2010 | Mehta | A61B 18/14 606/9 |
| 2010/0152725 A1* | 6/2010 | Pearson | A61B 18/12 606/33 |
| 2011/0118720 A1* | 5/2011 | Turner | A61B 18/1815 606/33 |
| 2013/0041369 A1* | 2/2013 | Godara | A61B 18/1402 606/34 |

OTHER PUBLICATIONS

Lokken, R Peter et al. Inflammatory Nodules Mimic Applicator Track Seeding After Percutaneous Ablation of Renal Tumours. American Journal of Roentgenology, 189: 845-848, Oct. 2007.
Goh, Pyt. Radiofrequency ablation of lung tumours. Biomedical Imaging and Intervention Journal, vol. 2, No. 3: e39, 2006.
Non-Final Office Action for U.S. Appl. No. 10/274,074 dated Mar. 23, 2005.
Final Office Action for U.S. Appl. No. 10/274,074 dated Oct. 14, 2005.
Non-Final Office Action for U.S. Appl. No. 10/274,074 dated Aug. 3, 2006.
Final Office Action for U.S. Appl. No. 10/274,074 dated Mar. 22, 2007.
Non-Final Office Action for U.S. Appl. No. 10/274,074 dated Aug. 3, 2007.
Final Office Action for U.S. Appl. No. 10/274,074 dated Feb. 14, 2008.
Final Office Action for U.S. Appl. No. 10/274,074 dated May 5, 2008.
Non-Final Office Action for U.S. Appl. No. 10/274,074 dated Jul. 25, 2008.

* cited by examiner

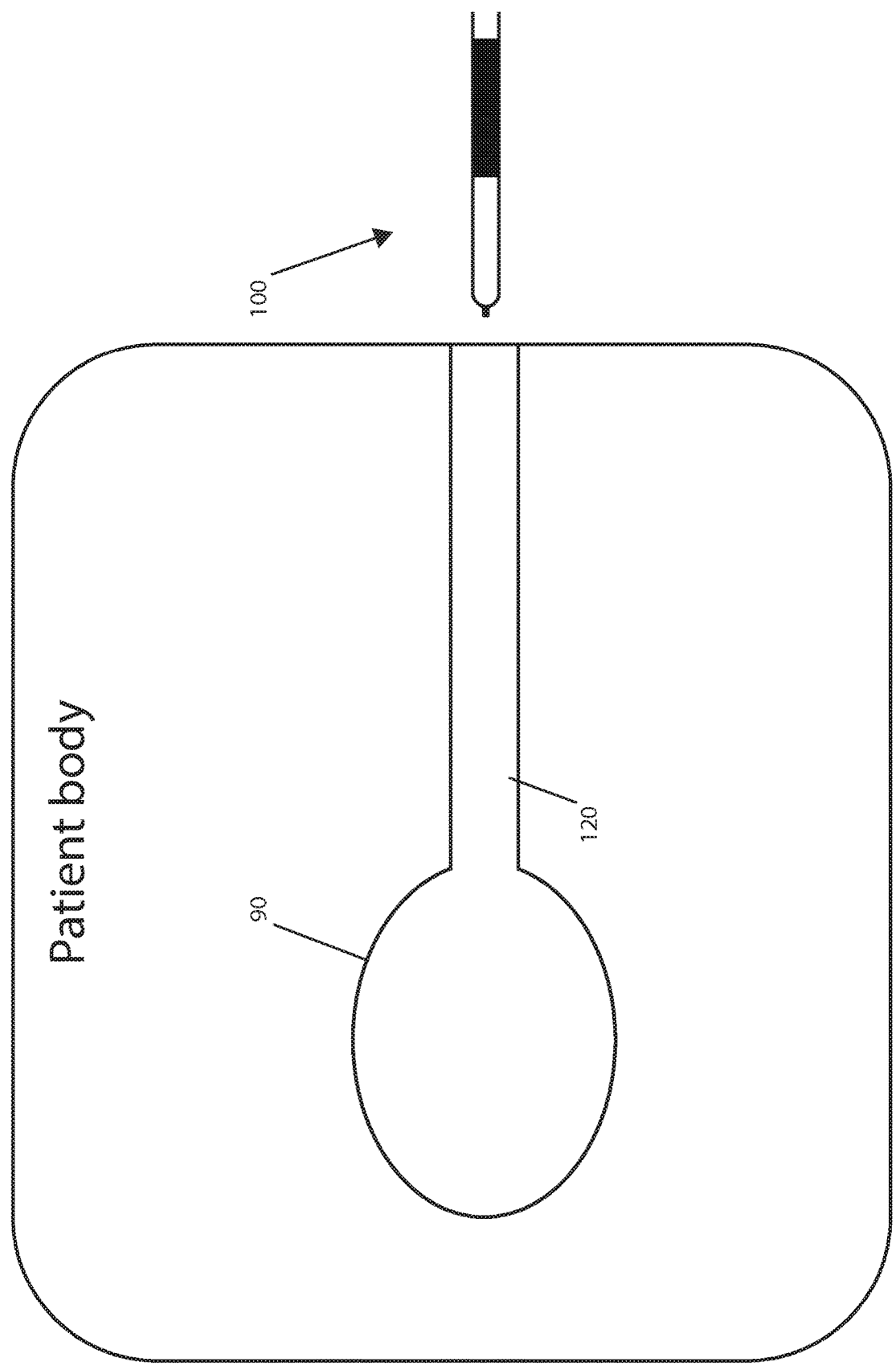

SYSTEMS AND METHODS FOR TRACK COAGULATION

CROSS-REFERENCES TO RELATED APPLICATIONS

The present application is a continuation of U.S. application Ser. No. 14/195,972 filed Mar. 4, 2014 (now U.S. Pat. No. 9,877,707); which claims the benefit of U.S. provisional application No. 61/774,213 filed Mar. 7, 2013; all of which are hereby incorporated by reference in their entirety.

TECHNICAL FIELD

The disclosure relates to an electrosurgical device and methods of use thereof. More specifically, the disclosure relates to an electrosurgical probe and methods of using the probe to prevent tumor seeding.

SUMMARY OF THE INVENTION

Tumor seeding may be prevented when withdrawing an energy delivery probe through a path that includes at least some bone tissue, by withdrawing the probe through the path while delivering energy in a bipolar manner to heat tissue surrounding the probe to a temperature sufficient to result in thermal coagulation necrosis of cells. The probe may be withdrawn incrementally or continuously. Examples of when such a method is useful include withdrawing a probe after ablating tissue or performing a biopsy.

In one broad aspect, embodiments of the present invention comprise a method of withdrawing a probe through a tissue via a path that traverses at least some bone tissue, the method including withdrawing the probe through the path, and at least partially concurrently delivering energy in a bipolar manner from the probe to heat a layer of tissue surrounding the probe to a temperature sufficient for thermal coagulation necrosis of cells.

As a feature of this broad aspect, some embodiments further comprise withdrawing the probe incrementally and measuring a temperature of the layer of tissue surrounding at least a portion of the path surrounding the probe prior to each incremental withdrawal to determine if the temperature is sufficient for thermal coagulation necrosis of cells.

In another broad aspect, embodiments of the present invention include a method of withdrawing a probe having an active tip through a tissue via a path, the method comprising: withdrawing the probe through the path in increments each having an increment length; and, for each incremental withdrawal, delivering energy from the active tip of the probe to heat a layer of tissue surrounding the probe to a temperature sufficient for thermal coagulation necrosis of cells to thereby define a coagulation volume, wherein the increment length is less than or equal to a length of the coagulation volume.

In yet another broad aspect, embodiments of the present invention include a method of withdrawing a probe having an active tip through a tissue via a path, the method comprising: continuously withdrawing the probe through the path while concurrently delivering energy from the active tip to heat a layer of tissue surrounding the probe; measuring a tissue parameter to confirm thermal coagulation necrosis of cells adjacent the probe; and adjusting a level of energy being delivered or a rate of probe withdrawal based on the measured tissue parameter.

Another broad aspect of an embodiment of the invention is directed towards a system including: an electrosurgical generator; at least one bipolar probe operable to be coupled to the electrosurgical generator, the at least one bipolar probe including at least one active electrode, at least one return electrode and at least one temperature sensor; and at least one introducer defining a lumen sized to receive the at least one bipolar probe; the generator being operable to: deliver electrical energy in a radiofrequency range; automatically detect at least one probe parameter of a probe coupled thereto; receive a measurement of at least one tissue parameter; substantially continuously adjust an energy delivery parameter in response to the at least one probe parameter and the at least one tissue parameter, the energy delivery parameter being selected from the group consisting of voltage and impedance; and provide an indication to a user when the at least one tissue parameter reaches a pre-determined threshold.

Certain embodiments of the present invention comprise a method of treating a tumor within a target tissue using an energy delivery probe, the method comprising the steps of (a) at least partially concurrently delivering energy from the energy delivery probe to ablate at least a part of the tumor and cooling the energy delivery probe with a probe cooling system; and (b) withdrawing the delivery probe incrementally through an entry/exit path and at least partially concurrently delivering energy from the energy delivery probe, with the probe cooling system turned off, to heat a layer of tissue surrounding and adjacent the probe to a temperature sufficient for thermal coagulation necrosis of cells in the layer of tissue.

As features of this aspect: in some embodiments, the energy delivery probe is a bipolar probe having fixed geometry electrodes; the method includes using an introducer (having markings for indicating a probe insertion distance) to advance the energy delivery probe to a tissue ablation treatment site; and step (b) further comprises coupling the energy delivery probe and introducer, and withdrawing the energy delivery probe and introducer by an incremental withdrawal distance equivalent to about a length of an active tip of the energy delivery probe.

Alternative embodiments of the present invention comprise a method of treating a tumor at least partially within a bone tissue using an energy delivery probe, the method comprising the steps of (a) at least partially concurrently delivering energy from the energy delivery probe to ablate at least a part of the tumor located within the bone tissue and cooling the energy delivery probe with a probe cooling system; and (b) withdrawing the delivery probe through an entry/exit path and at least partially concurrently delivering energy from the energy delivery probe, with the probe cooling system turned off, to heat a layer of tissue surrounding and adjacent the probe to a temperature sufficient for thermal coagulation necrosis of cells in the layer of tissue.

In further embodiments of the present invention, a method of treating a tumor at least partially within a bone tissue using an energy delivery probe is described. The method comprises the steps of (a) delivering energy from the energy delivery probe to ablate the tumor at least partially within the bone tissue; and (b) withdrawing the delivery probe incrementally through an entry/exit path and at least partially concurrently delivering energy from the energy delivery probe to heat a layer of tissue surrounding and adjacent the probe to a temperature sufficient for thermal coagulation necrosis of cells in the layer of tissue.

In yet further embodiments of the present invention, a method of withdrawing an energy delivery probe through a tissue via an entry/exit path that traverses at least some bone tissue is described. The method comprises withdrawing the probe through the path that includes at least some bone tissue and at least partially concurrently delivering energy in a bipolar manner from the probe to heat a layer of tissue surrounding the probe to a temperature sufficient for thermal coagulation necrosis of cells.

BRIEF DESCRIPTION OF THE DRAWINGS

In order that the invention may be readily understood, embodiments of the invention are illustrated by way of examples in the accompanying drawings, in which:

FIGS. 4a to 4c are schematic illustrations of a method in accordance with an embodiment of the present invention;

DETAILED DESCRIPTION

Figure 1:
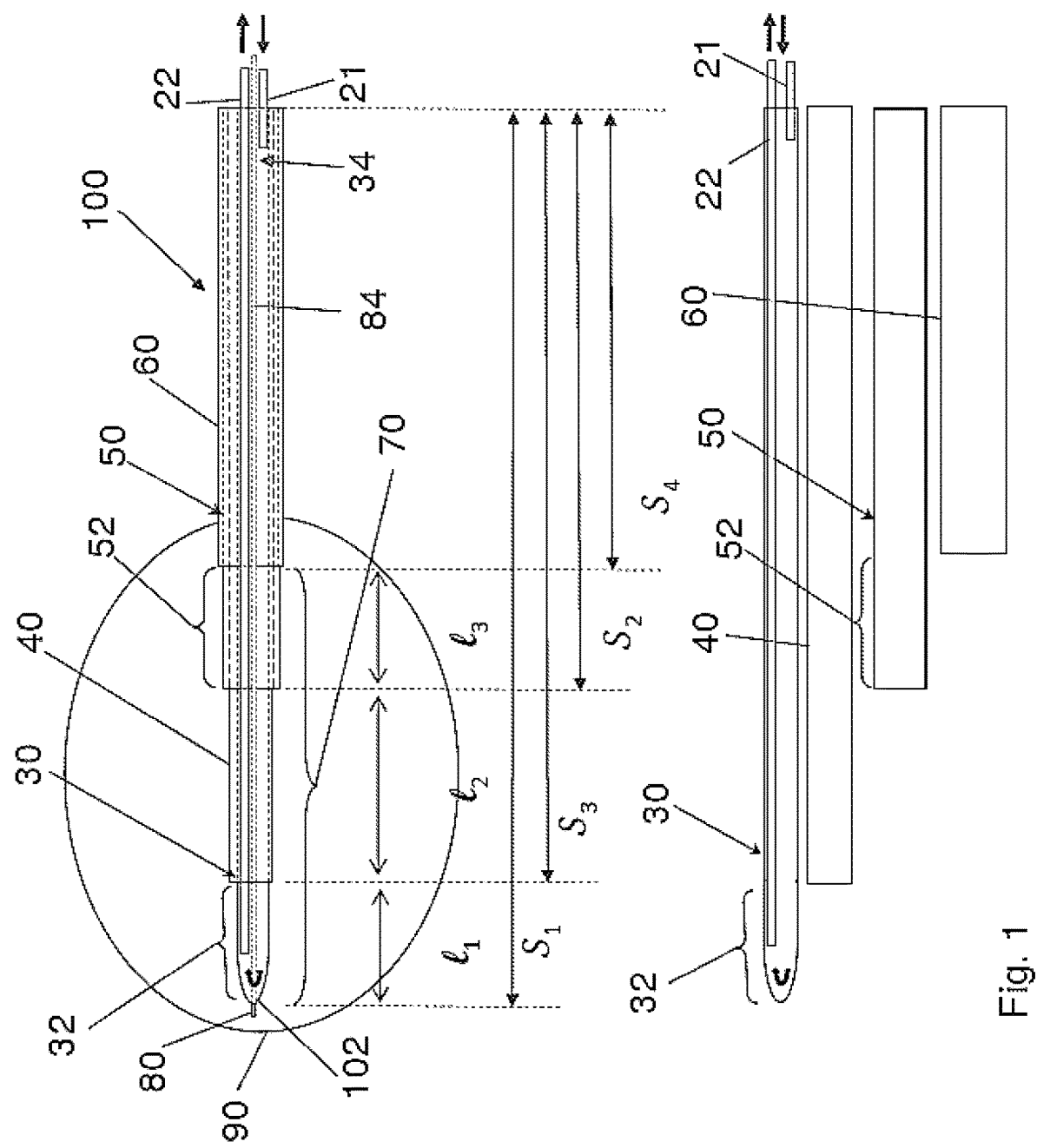
FIG. 1 is an illustration of a probe 100 in accordance with an embodiment of the present invention, showing various features in transparency for ease of illustration.

Radiofrequency-based devices are often used to ablate in soft tissues such as the liver in order to treat tumors located therein. Biopsy devices are often used to take samples from tumorous or possibly tumorous tissue. Following the procedure, a process of coagulating the tissue surrounding the insertion path of the device, sometimes referred to as track burning, may be used to reduce the chances of tumor seeding. However, ablating in bone tissue using an electrosurgical device for delivering electrical energy, and track burning when withdrawing the device, poses unique challenges due, for example, to the electrical properties of bone. The present inventors have discovered and reduced to practice various embodiments of a unique electrosurgical probe and methods of using the probe to coagulate the tissue surrounding the insertion path of the device.

In particular, the inventors have discovered that an electrosurgical probe structured to confine delivery of energy at its active tip (i.e. without requiring energy to flow to a grounding pad on the surface of a body) is particularly useful in a method for preventing tumor seeding when withdrawing the energy delivery probe through a path, the path including at least some bone tissue. The method comprises withdrawing the probe through the path while delivering energy in a bipolar manner from the probe to heat tissue surrounding the probe to a temperature sufficient to result in thermal coagulation necrosis of cells. The inventors have also discovered that, contrary to the delivery of energy during lesion formation, it is unpredictably advantageous to deliver energy without cooling (i.e. to disengage the cooling or turn it off) when using such a probe to coagulate a layer of tissue surrounding the probe's insertion and withdrawal path.

As an additional advantage of an embodiment of the present invention, a bipolar probe that has the active and return electrodes longitudinally displaced from each other on the same shaft (i.e. distal and proximal electrodes) will typically have a temperature distribution in the ablation zone with higher temperatures in relative proximity to the probe (especially when the cooling is turned off), when compared to monopolar devices that require an external grounding pad, whereby a single bipolar probe is operable to coagulate a thinner layer of tissue than a monopolar device.

In some embodiments, a bipolar probe having an active and a return electrode on a single shaft has a constant distance between the electrodes, referred to as a fixed or non-variable geometry, which provides for a relatively short and more predictable electrical flow pathway between electrodes than a system having a monopolar probe and a grounding pad. In a monopolar system, the pathway between the energy delivery electrode and grounding pad changes as the probe is withdrawn and, therefore, the pathway taken by the electrical current (and the types of tissue crossed) varies to a greater extent in monopolar procedures. Consequently, when track burning with a monopolar system, the variation in the different types of tissue crossed make it difficult to predictably/reliably achieve a consistent coagulation depth through the track (path of insertion/withdrawal). A single bipolar probe has more consistent energy flow because the electrode size, geometry, and distance of separation are typically fixed, and therefore the pathway through which the electrical current travels is better defined.

As a yet further advantage, in some embodiments, the probe includes a means for temperature monitoring which is particularly advantageous when used, for example, in tissue that hinders the predictability of lesioning, such as electrically insulative tissue including bone. A temperature-based algorithm for withdrawing a probe can include withdrawing the probe incrementally and measuring the tissue temperature prior to each incremental withdrawal to determine if the temperature is high enough for thermal coagulation necrosis of cells.

For some embodiments having distal and proximal electrodes, the temperature sensor (e.g. a thermocouple) is at or near the distal electrode. When energy is delivered by the probe when stationary, a volume of tissue around the electrodes and between the electrodes is heated to comprise a heated volume of tissue, with the space between the electrodes typically reaching the highest temperature. When the probe is withdrawn in a continuous manner, the tissue is first heated in the region of the heated volume around the proximal electrode, then in the region of the heated volume between the electrodes, and subsequently in the region of the heated volume around the distal electrode, whereby tissue surrounding the probe is typically hottest around the probe's distal electrode. When the probe is withdrawn in overlapping increments, the distal electrode starts each increment at a location that was heated during the previous increment. Temperature monitoring may aid in providing an effective amount of energy (sufficient but not excessive) to create a layer of coagulated cells adjacent the probe (sometimes referred to herein as simply "the path"). Temperature monitoring is beneficial for track burning through challenging anatomies, such as for example, when the entry/exit path goes through bone tissue or a transition zone from one type of tissue to another. Temperature monitoring is further beneficial for embodiments in which cooling is turned off during track burning to help prevent excess tissue coagulation.

In some such embodiments, the distal electrode is at the distal tip of the probe and the temperature sensor (e.g. a thermometer) is at the distal end of the distal electrode where the temperature is typically highest during withdrawal of the probe when track burning. This allows for more accurate control of the probe temperature at its hottest portion.

Thus, in one broad aspect of the present invention, a method is described for preventing tumor seeding when withdrawing a single energy delivery probe through a path, the path including at least some bone tissue. The method comprises withdrawing the probe through the path while delivering energy in a bipolar manner from the probe to heat tissue surrounding the path to a temperature sufficient to result in thermal coagulation necrosis of cells.

Furthermore, in another broad aspect of the present invention, a method for ablating a tumor in tissue and preventing tumor seeding when withdrawing the energy delivery probe is described. The method comprises delivering energy to ablate the target site with a probe cooling system turned on or activated and withdrawing the probe incrementally through the entry/exit path (the track) with the cooling system turned off or deactivated, while at least partially concurrently (i.e. overlapping in duration) delivering energy to heat tissue surrounding the probe to a temperature sufficient to result in thermal coagulation necrosis of cells adjacent the probe. In some such procedures, the tumor is at least partially in bone tissue. In some alternative embodiments, the procedure is performed by withdrawing the probe continuously, i.e. not incrementally. In other alternative embodiments, the procedure is performed without cooling the probe during ablation.

As used herein, the term "bipolar probe" is understood to mean a probe having an active tip including at least two electrically isolated electrodes whereby energy may be delivered between those electrodes in a manner which substantially confines the energy to an area substantially surrounding the active tip and obviates the need for a grounding pad or return electrode on the surface of a patient's body, thereby avoiding a flow of electrical energy through the patient's body from the active tip to such a grounding pad. Although the term "bipolar" is used herein, it should be understood to include other forms of energy delivery whereby energy flows substantially between electrodes located on the probe rather than to a grounding pad on the surface of the patient's body.

With specific reference now to the drawings in detail, it is stressed that the particulars shown are by way of example and for purposes of illustrative discussion of certain embodiments of the present invention only. Prior to explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
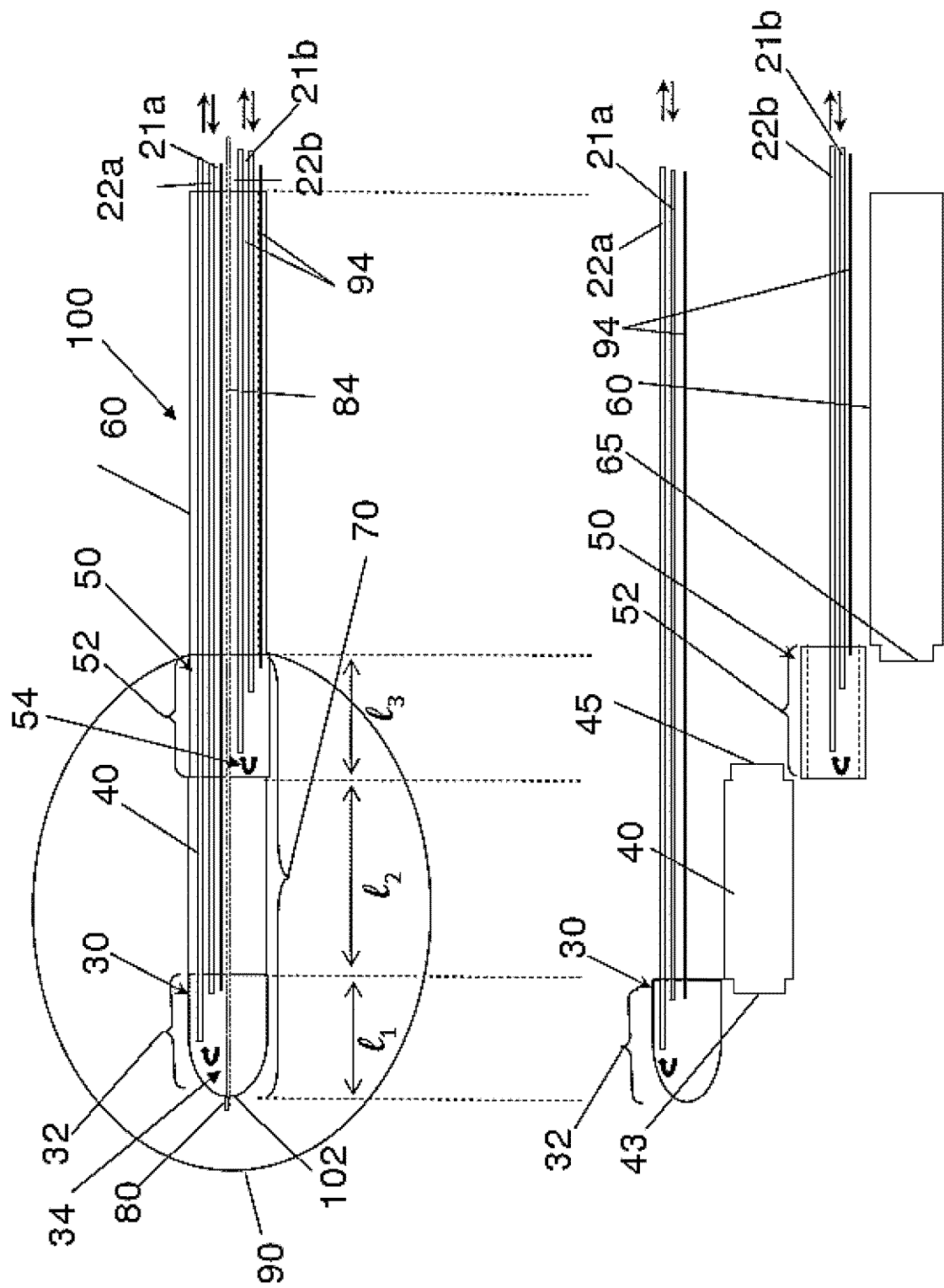
FIG. 2 is an illustration of a probe 100, in accordance with an alternate embodiment of the present invention, showing various features in transparency for ease of illustration.
Figure 3:
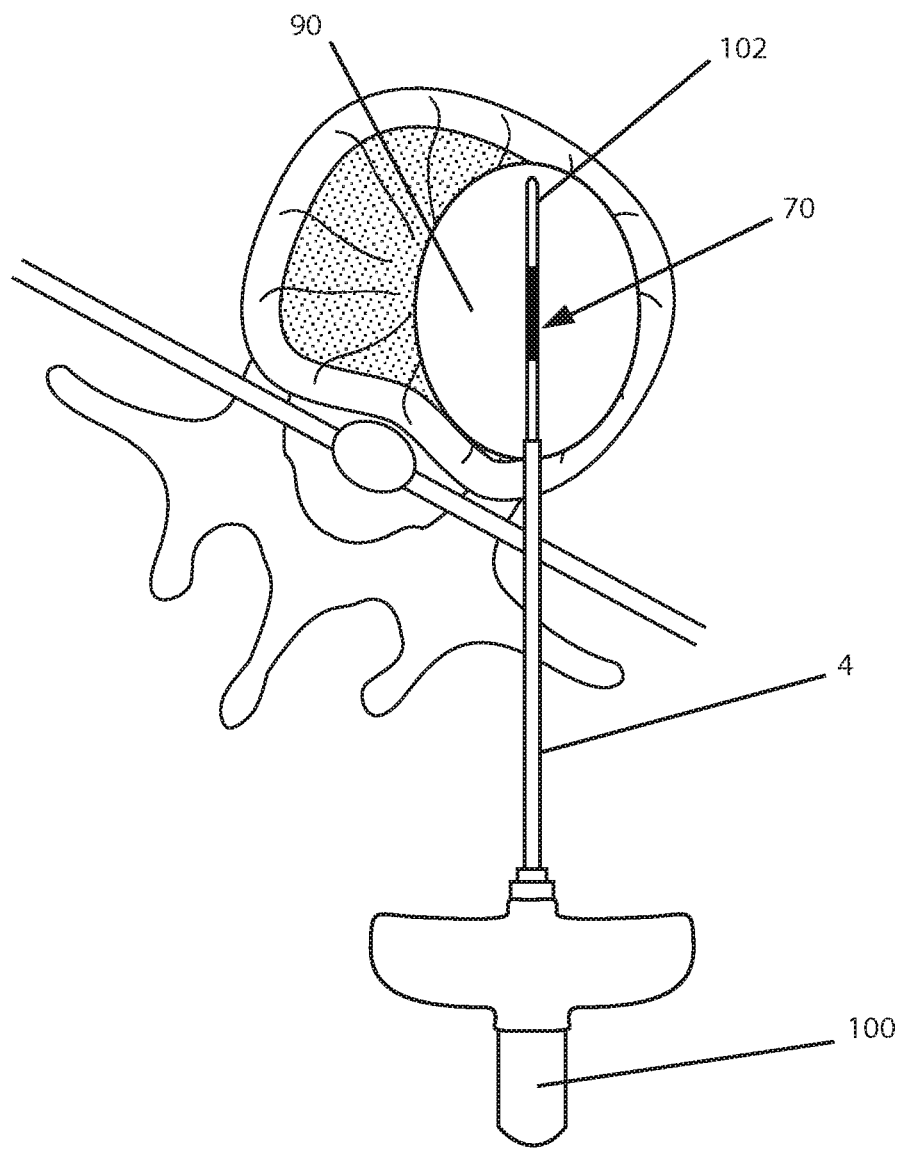
FIG. 3 is an illustration of an embodiment of a probe of the present invention positioned within an intervertebral disc.

FIGS. 1, 2 and 3—Probe Embodiments

FIG. 1 is an illustration of a probe 100. It is an example of a probe that may be used in accordance with some embodiments of the present invention. The probe comprises an inner elongate conductor 30 and an outer elongate conductor 50. The inner and outer conductors 30, 50 each have a hollow tubular configuration and define a lumen there-through. The inner and outer conductors 30, 50 are coupled to an energy supply at proximal ends thereof. In one example, the energy supply may comprise a radiofrequency (RF) energy delivery source and an energy sink. In one specific example, the inner conductor 30 functions as an active electrode and is coupled to an RF energy delivery source, and the outer conductor 50 is coupled to an energy sink such as a ground connection, forming a return electrode. In other words, the inner conductor 30 functions as a control electrode and the outer conductor 50 functions as a neutral or ground reference electrode. In another example, the outer conductor 50 functions as an active electrode and the inner conductor 30 functions as a return electrode. In such embodiments, probe 100 can be operated in a bipolar manner, where energy is delivered substantially between conductors 30, 50. The inner and outer conductors 30, 50 may be connected to the RF energy delivery source and ground via an electrical connection (not shown). The inner conductor 30 is disposed coaxially within the lumen of the outer conductor 50. The inner and the outer conductors 30, 50 each comprise an electrically conductive portion at least along a length thereof and more specifically, at least along a distal segment of conductors 30, 50. Each of the electrically conductive portions is coupled to an energy supply through an electrically conductive pathway.

The inner conductor 30 and the outer conductor 50 are electrically conductive along their length. In one example as shown in FIG. 1, the inner conductor 30 has a length S1, and the outer conductor 50 has a length S2. The inner conductor 30 is electrically isolated from the outer conductor 50 by an inner insulator 40 disposed between the inner conductor 30 and the outer conductor 50. In some embodiments, the inner insulator 40 extends longitudinally along at least the entire length of the outer conductor 50. In one example, as shown in FIG. 1, the inner insulator has a length S3 that is greater than length S2 of the outer conductor 50. In some embodiments, the inner insulator 40 is electrically insulative and thermally conductive. In the illustrated embodiments, the distal most portion of the inner conductor 30 is exposed at the distal tip thereof and forms a distal electrode 32 having a length L1.

The inner elongate conductor 30 as shown in FIG. 1 has a closed distal end thereof and defines a lumen 34 there-through for circulating a cooling fluid. The term "circulate" relates to fluid that mostly moves or is caused to move through a generally closed system in a controlled manner rather than fluid that enters and mostly passes through the system to the outside environment such as passing through an open ended tube. A fluid inlet tube 21 may be disposed within the lumen 34 to supply cooling fluid within the inner lumen 34 from a cooling supply (not shown). A fluid outlet tube 22 may be disposed alongside the fluid inlet tube 21 within the inner lumen 34 to allow the cooling fluid to exit via a proximal end of the probe 100. The outer conductor 50 has an insulator 60 that is electrically insulative disposed on an outer surface thereof, along at least a portion of the outer conductor 50, whereas a distal portion of the outer conductor 50 remains electrically exposed, forming a proximal electrode 52 with a length L3. In one example, the outer insulator 60 has a length S4 as shown in FIG. 1. In one embodiment the outer insulator 60 may have a length that is substantially the same as the length of the outer conductor 50. The inner insulator 40 is exposed between the distal edge of the proximal electrode 52 and the proximal tip of the distal electrode 32. The length of the exposed insulator is labeled as L2. The region of the probe extending from the proximal electrode 52 to the distal electrode 32 forms an active tip 70. A radiopaque band (not shown) may be positioned at a proximal end of the active tip 70. The radiopaque band may act as a navigational reference to guide and facilitate in positioning of the active tip 70 at a target location within a patient's body. In other embodiments, the radiopaque band may be positioned at any location along the active tip 70 or at any location along the probe 100. In still another embodiment, more than one radiopaque band or a radiopaque marker may be positioned along the probe. In one example the radiopaque band may function as a navigational reference under fluoroscopic imaging.

In one example, the proximal electrode 52 is a return electrode and the cooling fluid cools the proximal electrode 52 prior to reaching and cooling the distal electrode 32, which is the active electrode. This may provide a more uniform lesion to be produced when RF energy is supplied to the probe 100.

In one embodiment the active tip 70 may have a length (L1+L2+L3) that ranges from about 5 mm to about 40 mm. In one example, the length of the distal electrode 32 (L1), the exposed inner insulator 40 (L2), and the proximal electrode 52 (L3) may vary in about a 2:1:2 ratio. In other embodiments the ratio may be in about a 1:1:1 configuration. Alternate embodiments are possible as well. In other embodiments, the lengths L1, L2 and L3 may have a different ratio. In another example, the L1:L2:L3 ratio is about 7:6:7.

In another embodiment, the inner and outer conductors 30, 50 may only extend along a portion of the probe 100. In one specific example, as shown in FIG. 2, inner and outer conductors 30, 50 may be electrically conductive along their lengths thereof and may form the proximal and the distal electrodes, 32 and 52. Only the exposed portions of the inner and outer conductors 30 and 50 are electrically conductive and the inner and outer conductors 30, 50 may have substantially the same width. The inner and outer conductors may be spaced apart and electrically isolated from each other by an inner insulator 40. In one example the inner insulator 40 may comprise a polymer. In a specific example, the insulator 40 may comprise a substantially rigid plastic insert. In one example the electrically isolated distal and proximal electrodes 32 and 52, may be cooled through separate cooling sources. As shown in FIG. 2, the distal electrode 32 is supplied with a cooling fluid through fluid inlet and outlet tubes 21a and 22a. Whereas, cooling to the proximal electrode 52 is supplied through cooling inlet and outlet tubes 21b and 22b. The fluid inlet and outlet tubes may comprise a non-conductive material such as a polymer. Each of the proximal and distal electrodes 52, 32 are coupled to an energy supply through electrically conductive insulated wires 94.

In this example, as shown in FIG. 2, the distal and proximal electrodes 32 and 52 each define a closed inner lumen 34 and 54 respectively within which cooling fluid flows. The distal electrode 32 has a closed distal end and a closed proximal end formed by co-operative engagement of the distal electrode proximal portion with a distal face 43 of the inner insulator 40, defining the closed inner lumen 34. The proximal electrode 52 has a closed distal end formed by co-operative engagement of the proximal electrode distal end with the proximal face 45 of the inner insulator 40. The proximal electrode 52 further has a closed proximal end defined by co-operative engagement of the proximal electrode proximal end with a distal face 65 of the outer insulator 60, defining the closed inner lumen 54. The cooling fluid is restricted within the lumens 34 and 54. The distal face 65 of the outer insulator, as well as the distal face 43 and the proximal face 45 of the inner insulator, extend substantially transversally along the width of the probe. The distal face 65 may comprise openings to allow fluid inlet tubes 21a, 21b and fluid outlet tubes 22a, 22b as well as insulated wires 94 to extend therethrough. Similarly, distal and proximal faces 43 and 45 may provide openings therethrough to allow passage of the inlet and outlet tubes 21a and 21b respectively and one of the insulated wires 94.

Additionally, a temperature sensor 80 may be positioned at a location along the probe 100 as shown in FIGS. 1 and 2. In one embodiment the temperature sensor 80 may be positioned substantially adjacent the distal tip 102 of the probe 100. For example, the temperature sensor 80 may protrude from the surface of the distal electrode 32. In other words, temperature sensor 80 may jut out or stick out from a surrounding surface of the probe 100. In other embodiments the temperature sensor 80 may be positioned at any location along the length of the probe. In some embodiments the temperature sensor 80 may be positioned at or adjacent to the active tip 70. In one example, the temperature sensor 80 may comprise a thermocouple. In one specific example, a thermocouple may be formed using a hypotube 84 disposed within the lumen 34 of the inner conductor 30. A constantan wire can be disposed within the thermocouple hypotube 84 to form a thermocouple junction (not shown) about the distal tip 102. In other embodiments, a thermocouple may be formed using a pair of wires to form a junction. In one example, a thermocouple is positioned at a distal face of the proximal electrode 52. In another example, a thermocouple is positioned between the proximal electrode 52 and inner insulator 40. In one example, the temperature sensor 80 is coupled to and in communication with a controller for the energy supply, for example the energy supply having an RF energy delivery source. In one example, the temperature sensor 80 may be coupled to a controller at its proximal end via a handle.

In some embodiments, a second temperature sensor is proximate to proximal electrode 52 and is in communication with a controller for the energy supply for providing additional information. Such an embodiment could be used with a generator capable of monitoring two temperature sensors at one time. Alternatively, a generator capable of monitoring only one temperature at a time could be used if an external device swapped between the two (or more) temperature sensors. Further details regarding the structure and use of some probe embodiments that may be used in the method of the present invention may be found in PCT application PCT/CA2011/050203, filed Apr. 15, 2011, and hereby incorporated by reference in its entirely.

FIG. 3 is illustrates an example of the use of probe 100. In this particular embodiment, an introducer needle assembly 4 is inserted and advanced to a target location within a patient's body. The introducer needle assembly may comprise a cannula with a stylet disposed therein. In the example of FIG. 3, the target location is a vertebral body. Once the introducer needle assembly 4 has been positioned at the target site, the stylet is withdrawn from the cannula. The probe 100 is then inserted through the cannula and advanced to the target site. RF energy may be delivered in a bipolar manner between electrodes 32 and 52 to allow a lesion to form adjacent the active tip 70 at the target location 90 within the vertebral body.

Figure 4A:
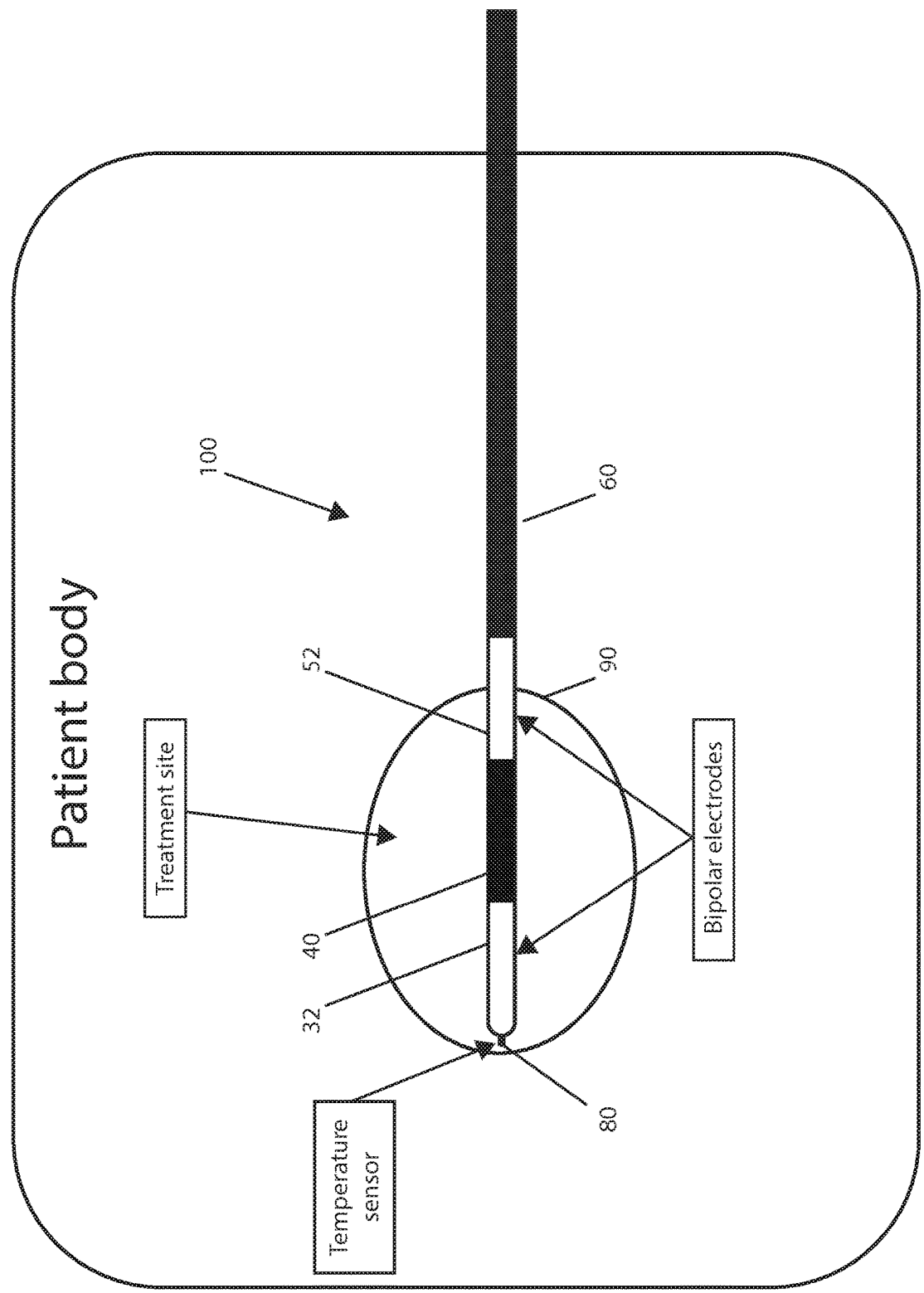
Figure 4B:
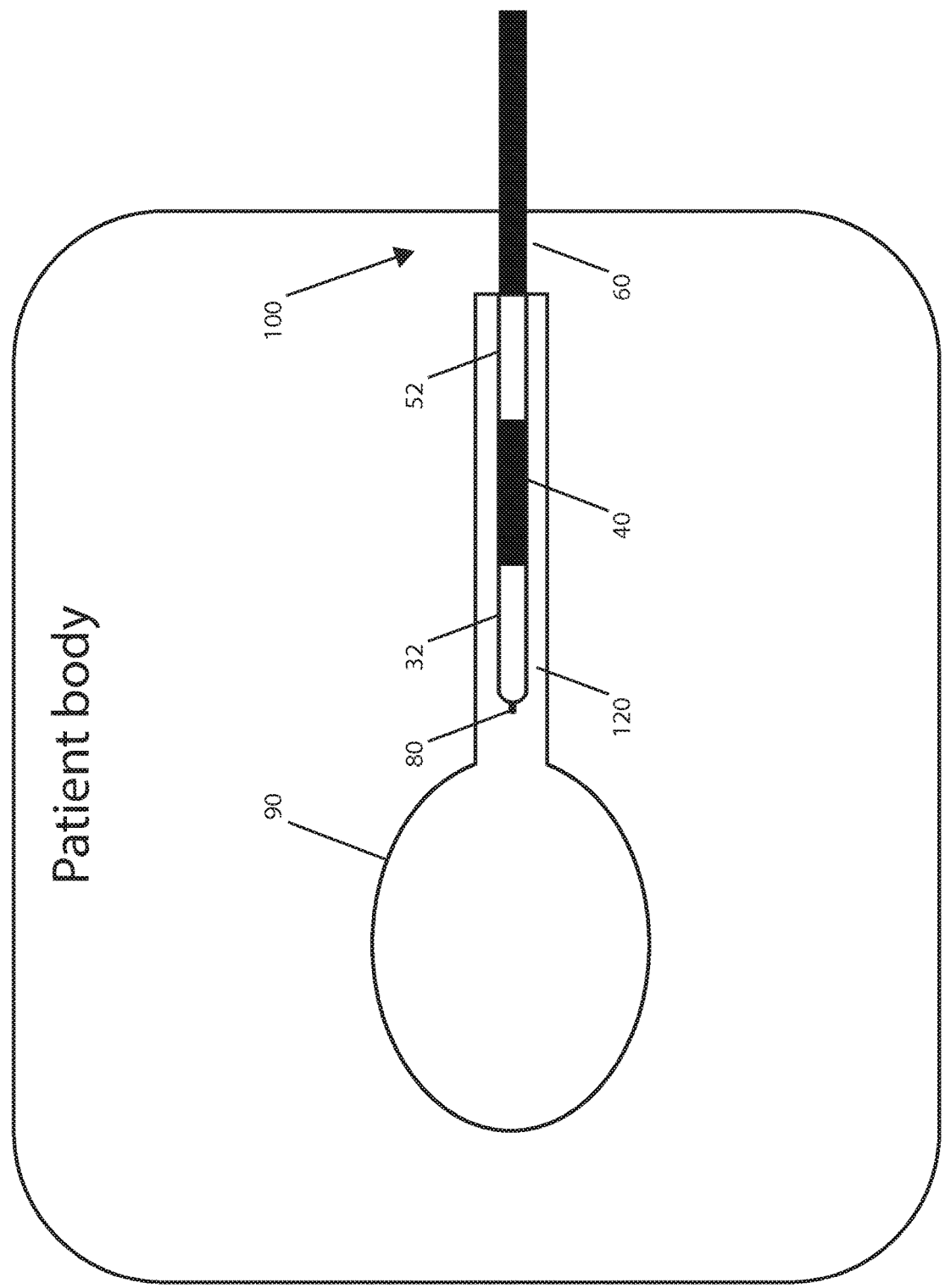

FIGS. 4a to 4c: Two Stage Treatment Method

FIGS. 4a to 4c illustrate a two-stage method of treating a tumor in a tissue. FIG. 4a shows the first stage, which comprises lesioning a tumor. FIG. 4b shows the tissue surrounding the entry/exit path of probe 100 being coagulated (i.e. track burning), which typically includes the probe cooling system being turned off. FIG. 4c represents a completed procedure, with probe 100 outside of the patient's body. FIGS. 4a to 4c are illustrative of the basic concept of track burning and do not show an introducer assembly which is typically used.

FIG. 4a shows a lesion at a target location 90, the lesion being formed by energy flowing in a bipolar manner between distal electrode 32 and proximal electrode 52, as previously described with reference to FIGS. 1 to 3. The probe's active tip is typically cooled during lesioning, and the tissue temperature is measured using temperature sensor 80. Probe 100 also includes outer insulator 60 and inner insulator When the lesion is completed, the probe cooling system is turned off i.e. the flow of cooling fluid is stopped. Probe 100 is withdrawn with energy still being supplied to the active electrode. Because the cooling system is turned off, tissue close to the probe heats faster than it would with the probe cooling system turned on. Consequently, as the probe is withdrawn it coagulates tissue closer to the probe than it would with cooling, as represented by track burn 120 of FIG. 4b. During a typical track burning procedure, a thin layer of tissue is heated and coagulated. An introducer assembly is withdrawn with probe 100 such as to leave electrodes 32 and 52 exposed and in contact with the tissue surrounding probe 100. The temperature of the tissue surrounding the entry/exit path is measured using temperature sensor 80 to ensure the temperature is sufficient for coagulation necrosis of cells. Probe 100 may be withdrawn in a series of incremental withdrawals (i.e. the probe is stopped after each increment and is not withdrawn in a continuous manner), with the temperature being measured before each incremental withdrawal. In alternative embodiments, probe 100 can be withdrawn at a steady pace in a continuous manner.

In FIGS. 4a to 4c, the patient's body is represented by a large rectangular shaped box. In FIG. 4c, the track burn extends to the edge of the patient's body (the skin layer) and probe 100 has been withdrawn to outside of the patient's body. The typical physiological range of impedance is under 1000 for the disclosed probes (i.e. for probes having the disclosed geometries). Tissue electrical conductivity (impedance) is constantly measured as the probe is being withdrawn from the patient to identify when the impedance is above the physiological range (i.e. when the probe is outside of the body). In some embodiments, an impedance measurement above 1000 ohms is taken as indicating that the probe is out of the patient's body, while in some other embodiments, an impedance in the range of 1000-3000 ohms is taken as indicating that the probe is out of the patient's body. Energy delivery is stopped after complete removal of probe 100 from the patient's body is detected. In some alternative embodiments, energy delivery is stopped after a fixed time period.

One embodiment of a two-stage treatment as described above is a method of treating a tumor within a target tissue using an energy delivery probe 100 comprising the steps of: (a) at least partially concurrently delivering energy from the energy delivery probe 100 to ablate at least a part of the tumor and cooling the energy delivery probe with a probe cooling system; and (b) withdrawing the delivery probe 100 incrementally through an entry/exit path and at least partially concurrently delivering energy from the energy delivery probe 100, with the probe cooling system turned off, to heat a layer of tissue surrounding and adjacent the entry/exit path to a temperature sufficient for thermal coagulation necrosis of cells in the layer of tissue.

Another embodiment of the above described treatment procedure includes cooled ablation of a target site located at least partially within bone tissue followed by uncooled probe retraction, where the withdrawal is typically substantially continuous, i.e. not incremental. For example, a method of treating a tumor at least partially within a bone tissue using an energy delivery probe may comprise the steps of: (a) at least partially concurrently delivering energy from the energy delivery probe to ablate at least a part of the tumor at least partially within the bone tissue and cooling the energy delivery probe with a probe cooling system; and (b) withdrawing the delivery probe through an entry/exit path and at least partially concurrently delivering energy from the energy delivery probe, with the probe cooling system turned off, to heat a layer of tissue surrounding and adjacent the probe to a temperature sufficient for thermal coagulation necrosis of cells in the layer of tissue.

A still further embodiment or application of such a treatment procedure does not include delivering a cooling fluid during the ablation portion of the procedure. Typically, such embodiments include ablation of a target site at least partially within bone tissue, followed by probe retraction or withdrawal along with incremental track burning. An example of such an embodiment is a method of treating a tumor at least partially within a bone tissue using an energy delivery probe comprising the steps of: (a) delivering energy from the energy delivery probe to ablate the tumor at least partially within the bone tissue; and (b) withdrawing the delivery probe incrementally through an entry/exit path and at least partially concurrently delivering energy from the energy delivery probe to heat a layer of tissue surrounding and adjacent the probe to a temperature sufficient for thermal coagulation necrosis of cells in the layer of tissue.

Figure 5A:
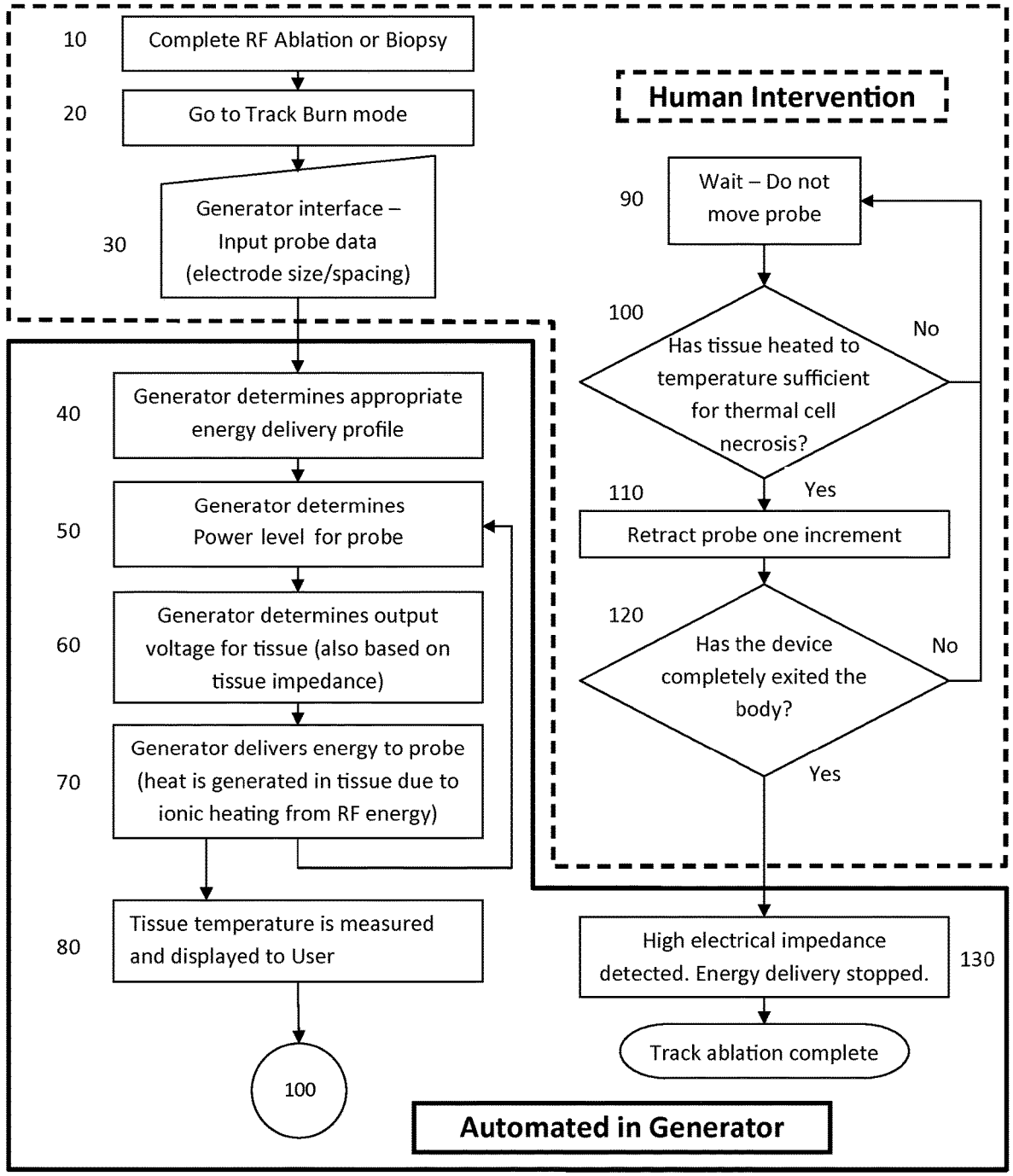
FIGS. 5a and 5b are flow charts of alternate embodiments of a method of the present invention.
Figure 5B:
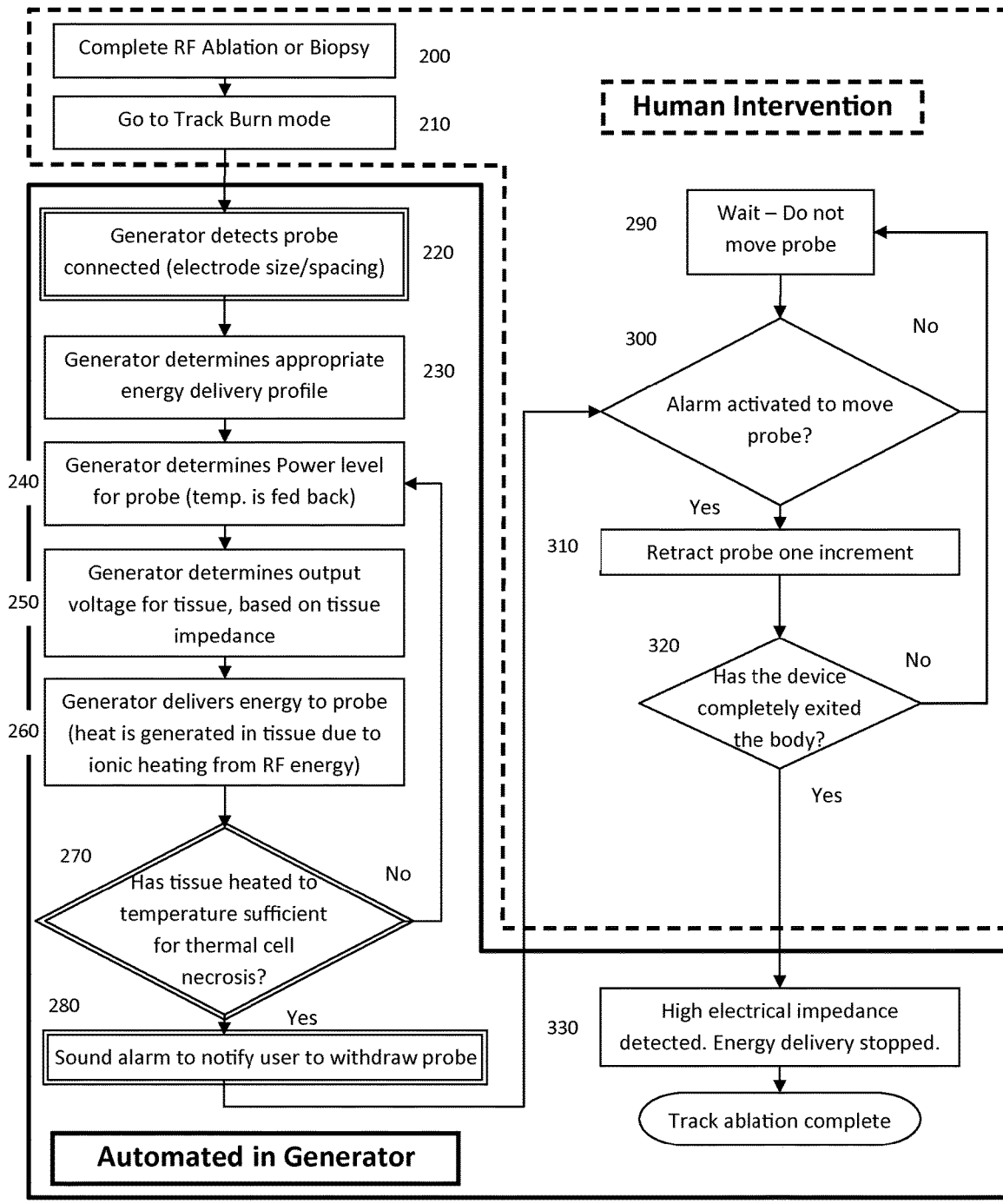

FIGS. 5a and 5b: Track Burning Embodiments

FIGS. 5a and 5b are flow charts representing two embodiments of methods of track burning. FIG. 5a shows a power level controlled embodiment in which the physician determines when to move a probe. FIG. 5b shows a temperature controlled embodiment in which an alarm or alert signal communicates to the physician when to move a probe. Such an embodiment, when used in conjunction with a robotics-based surgical system, may also allow the probe withdrawal to be completely automated.

The first step of FIG. 5a (step 10) is completing the ablation stage of the two stage procedure previously described. In alternative embodiments, step 10 comprises completing a biopsy procedure i.e. the method of FIGS. 5a (and 5b) may also be used for track burning after a biopsy procedure. Step 20 is for switching a generator from ablation mode to track burn mode, which includes turning off the probe cooling system. An appropriate generator for performing track burning is the Pain Management PMG-TD generator (Kimberly-Clark Corporation). Step 30 is for entering probe data, such as electrode size and spacing, into the generator through an interface. The interface may be part of the generator, the probe, or some other device e.g. a computer. Step 40 comprises determining the appropriate energy delivery level/profile based on the data input in step 30. The profile is determined by an algorithm of the generator, for example using a lookup table, as are the values determined in steps 50 and 60. Step 50 is for determining the power level of the energy to be supplied to the probe for delivery to tissue. Step 60 comprises determining the voltage of the energy for delivery to tissue. The power level (step 50) and the output voltage (step 60) are also functions of measured impedance of tissue, as explained below.

In some embodiments, represented by FIG. 5a, the power is maintained substantially constant after an initial ramp-up period while the voltage varies during the procedure. Step 70 includes delivering RF energy to tissue surrounding the probe's entry/exit path, which causes the tissue to heat up and ablates a layer of tissue along the entry/exit path. The feedback loop from step 70 to step 50 represents ongoing feedback to the generator related to changes in impedance of the tissue surrounding the probe's entry/exit path. The generator continuously monitors the impedance level to fine-tune the voltage output needed to achieve or maintain a given power level (P=V.sup.2/R). Step 50 uses the impedance as an input to calculate a power level of energy and step 60 uses the power level and impedance to determine the voltage of the energy delivered to the tissue. Also, if impedance is too high, energy delivery is stopped (step 130). Step 80 is for measuring the temperature (of the tissue being heated) and displaying the temperature to a user. Step 80 branches to step 100 which is part of the steps shown in the right hand side of the flowchart. In the embodiment of FIG. 5a, steps 40 to 80 take place in the generator. In alternative embodiments, some of the steps could be performed using an external device, e.g. an external computer determining some of the values.

The flowchart of FIG. 5a shows steps 10 to 30, and 90 to 120 as including human intervention i.e. a user is involved in performing the steps. Step 100 comprises the user deciding if the probe should be moved or kept stationary based on the temperature measured in step 80. If the temperature is not sufficient for thermal cell necrosis (i.e. the decision is no), the procedure loops back to step 90 which comprises waiting and keeping the probe still/maintaining the position of the probe. After waiting, the procedure then again proceeds to step 100 and the user checks the temperature. If the decision in step 100 is yes, the procedure advances to step 110. Step 110 is for retracting the probe by one increment. The length of the increment may be, for example, less than a length of the active tip of the probe, to allow for partial overlap of ablations along the track. After the increment of step 110, the procedure goes to step 120, which is for determining if the probe has exited the body. The user can make this determination visually. If the device has not exited the body, the procedure may go back to step 90 (waiting and keeping the probe stationary). If the probe has exited the patient's body, the procedure advances to step 130. Step 130 includes high impedance being detected, which causes the generator to stop delivering energy. Some embodiments use an impedance limit of 1000 ohms to stop energy delivery. The user could also switch the energy delivery off. Once energy delivery has stopped, the procedure is completed.

The first step of FIG. 5b (step 200) is for completing the ablation stage previously described with reference to FIGS. 4a to 4c. In alternative embodiments, step 200 comprises completing a biopsy procedure as described hereinabove with respect to FIG. 5a. Step 210 includes switching a generator from ablation mode to track burn mode, which includes turning off the probe cooling system. Step 220 is for detecting probe data, which typically includes electrode size and spacing. The probe data may be detected by the generator or a device external to the generator, for example using an identifier associated with the probe. Step 230 comprises determining the appropriate energy delivery level/profile based on the data detected in step 220. Step 240 is for determining the power level of the energy to be supplied to the probe for delivery to tissue. The power level is also a function of the temperature measured in step 270 (explained below). Step 250 comprises determining the voltage of the energy to be delivered from the probe to tissue. Typically, the voltage is determined by an algorithm in the generator, as are the values determined in steps 230 and 240.

In some embodiments represented by FIG. 5b, the temperature is kept substantially constant after an initial ramp-up period while the power varies during the procedure. Step 260 includes delivering energy to tissue surrounding the probe entry/exit path, which causes the tissue to heat up. Step 270 is for measuring the temperature (of the tissue being heated). If the temperature is not sufficiently high for thermal cell necrosis, the information is fed back to step 240 to be used in determining or adjusting the power level. If the temperature is high enough for thermal cell necrosis, the procedure advances to step 280 which comprises communicating an alert signal to a user to indicate that the user should move the probe. The alert signal may be an audible indicator such as an alarm, a visual indicator such as a light or any other suitable means for alerting a user. In some embodiments, the temperature is at least 60.degree. C. when the indicator alerts and/or signals to the user that the temperature is sufficient for thermal coagulation necrosis. The alert signal output of step 280 branches to step 300 which is part of the steps shown on the right hand side of the FIG. 5b. In the embodiment of FIG. 5b, steps 220 to 280 and 330 take place in the generator. In alternative embodiments, some of the steps could be performed using an external device, e.g. an external computer determining some of the values.

The flowchart of FIG. 5b shows steps 200 and 210, and 290 to 320 as including human intervention i.e. a user is involved in performing the steps. In alternative embodiments, one or more of these steps may be automated, for example by using a robotic surgery system to automatically move the probe in response to a signal from the generator. Step 300 comprises the user determining whether or not the alert signal (e.g. an alarm) is indicating that the probe should be moved. If the temperature is not sufficient for thermal cell necrosis, the alarm does not sound (i.e. the decision is no), the procedure loops back to step 290 which comprises waiting and maintaining the position of the probe until an alert signals that the temperature is high enough, whereby the procedure advances to step 300. When the decision in step 300 is yes, the procedure proceeds to step 310. Step 310 is for retracting the probe by one increment, as described hereinabove. After the incremental withdrawal of step 310, the procedure advances to step 320, which is for determining if the probe has exited the body. The user may make this determination visually. If the device has not exited the body, the procedure returns to step 290 and the user waits and keeps the probe stationary. If the probe has exited the patient's body, the procedure advances to step 330. Step 330 includes high impedance being detected, which causes the generator to stop energy delivery. In some embodiments, steps 320 and 330 occur simultaneously, i.e. the generator determines that the probe has exited the body by measuring the impedance. The user may alternatively switch the energy delivery off manually. Once energy delivery has stopped, the procedure is completed.

Alternative embodiments of track burning include using feedback based on monitoring the impedance (instead of temperature). Such embodiments comprise incrementally withdrawing the probe when the impedance increases beyond a certain threshold (mid-range impedance). A relatively low impedance level indicates tissue is not coagulated, mid-range impedance level indicates a track has been burned, and a high-range impedance level indicates the probe is out of the patient's body and the procedure should be stopped.

Figure 6:
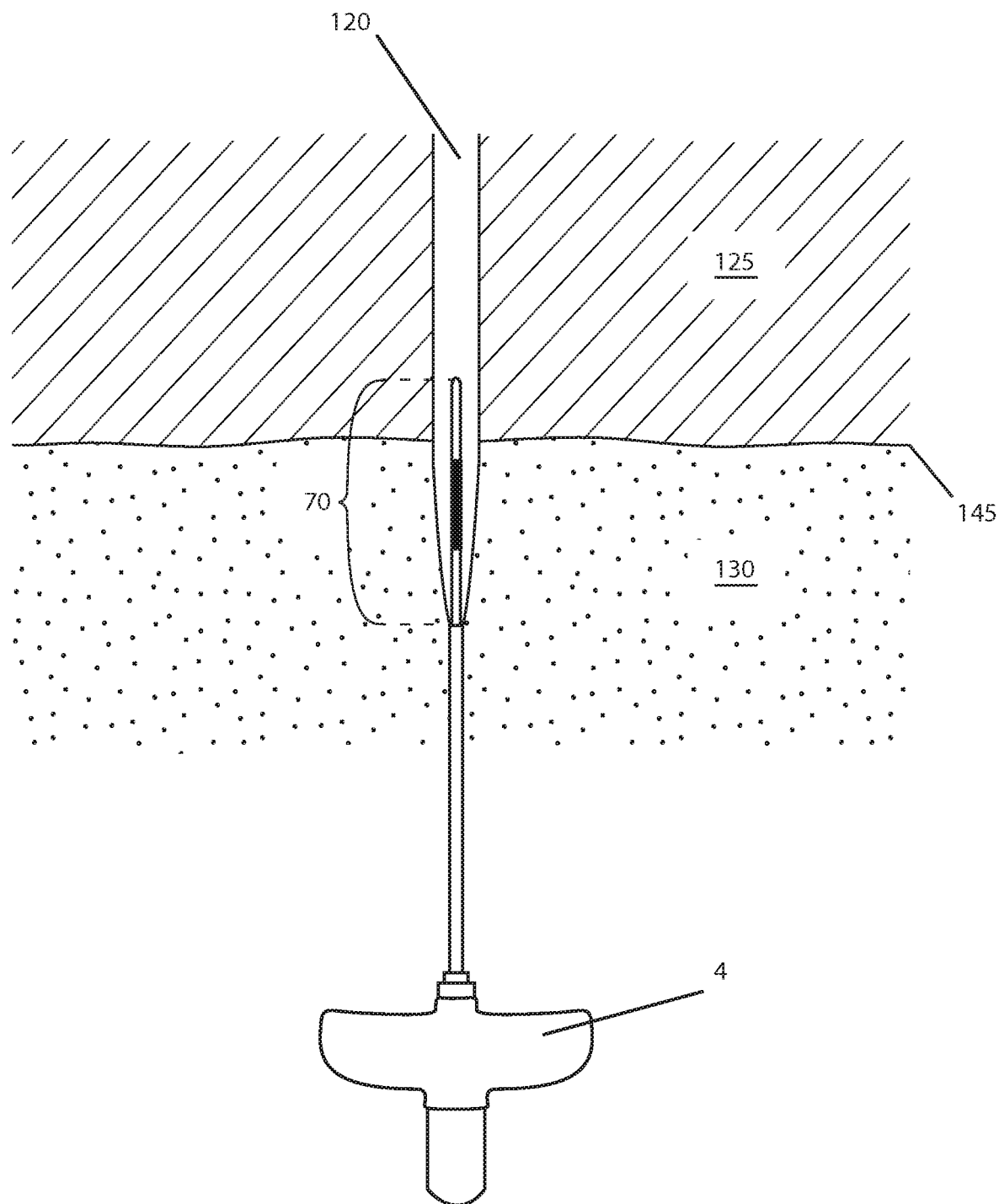
FIG. 6 is an illustration of an embodiment of a probe of the present invention, in use.

FIG. 6: Track Burning Through Different Types of Tissue

Probe 100 may be used to treat a region within a patient's body comprising tissue with varying composition, including soft tissues and hard tissues such as bone. FIG. 6 illustrates a coagulated tissue path 120 through hard tissue 125, soft tissue 130, and tissue boundary 145. Different types of tissues have different heat and electrical conductivities which result in there being different heat flow patterns/paths during energy delivery. For example, because bone tissue is a less effective heat conductor than soft tissue, heat will dissipate more rapidly in the soft tissue.

Furthermore, different types of tissue heat at different rates, leading to the probe being withdrawn at different rates depending on tissue type, e.g. a tissue that heats quickly (relative to a slow heating tissue), has less time between incremental withdrawals such that the probe is withdrawn more rapidly in a tissue that heats quickly than in a slow heating tissue. In general, different heat conductivities create unpredictability in track burning.

In some such applications, a method of track burning along a path including at least some bone tissue is used. The method includes using a bipolar probe with electrodes spaced apart on one shaft to provide a heat flow pattern in which the heat flows substantially proximate the probe shaft. Some embodiments include withdrawing the probe in incremental withdrawals and measuring the temperature before each incremental withdrawal to check for an adequate temperature for cell coagulation. Some embodiments of this method also include track burning with the probe cooling system turned off. Some specific embodiments include the use of a distal tip heat sensor, such as heat sensor 80 of FIG. 1, to enable sufficient but not excessive heating.

In one specific embodiment, a method of withdrawing an energy delivery probe 100 through tissue via an entry/exit path that traverses at least some bone tissue, includes withdrawing the probe 100 through the path and at least partially concurrently delivering energy in a bipolar manner from the probe 100 to heat tissue surrounding the entry/exit path to a temperature sufficient for thermal coagulation necrosis of cells. In some such embodiments, at least a portion of the entry/exit path is surrounded by and adjacent to bone tissue. In some embodiments, the entry/exit path traverses a tissue transition zone from one type of tissue to another type of tissue.

Figure 8:
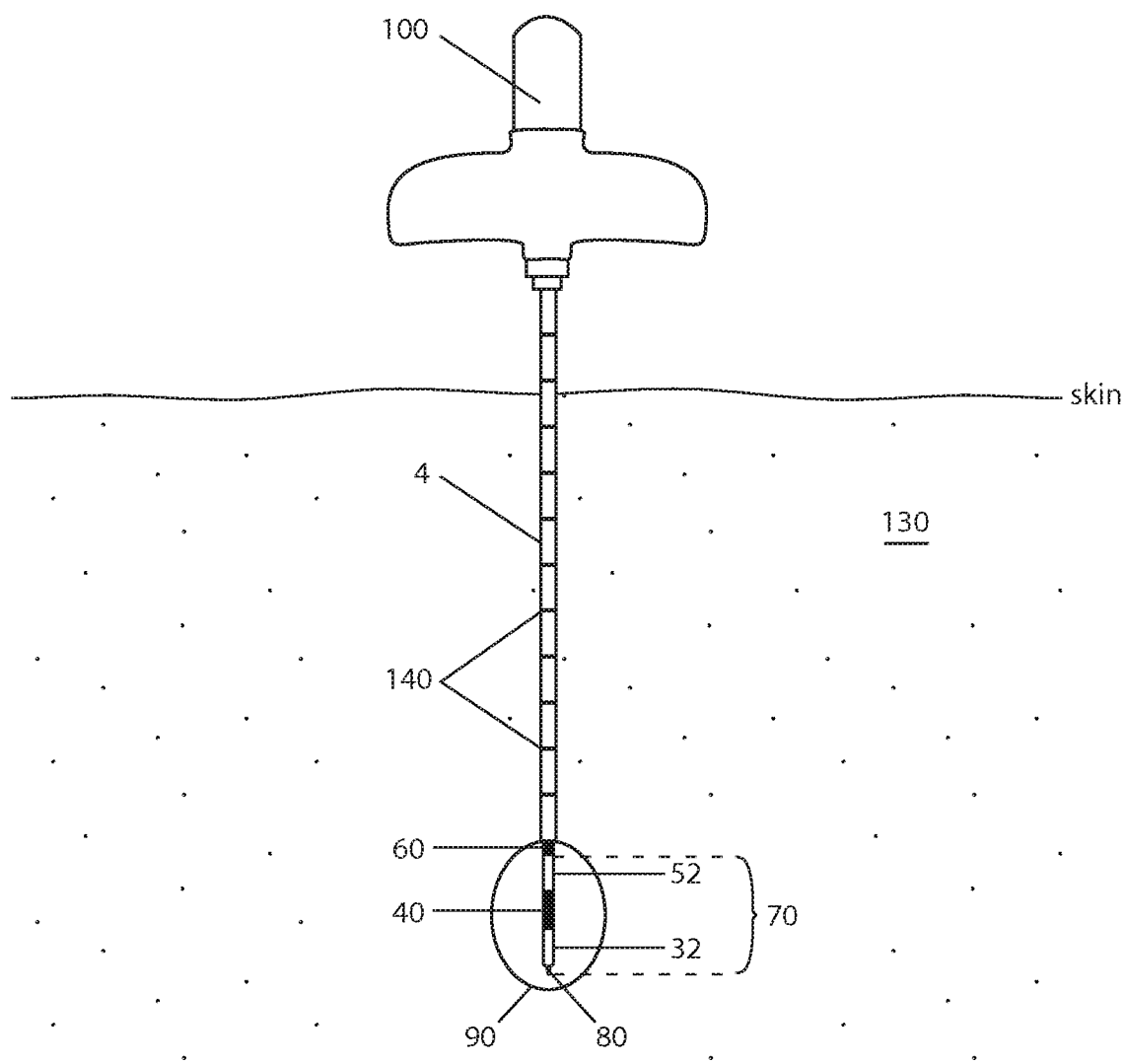
FIG. 8 is an illustration of a probe and introducer, in accordance with an alternate embodiment of the present invention, positioned within tissue of a patient's body.

FIG. 8: Probe and Introducer with Markings

Some embodiments include using an introducer needle assembly for track burning, the introducer needle assembly including markings. One such embodiment is for a method using a bipolar probe with fixed geometry electrodes, the method including withdrawing the probe in short incremental withdrawals that result in overlapping coagulation volumes. When the probe is being withdrawn in increments, the temperature of the tissue surrounding the distal electrode normally very hot as it has previously been heated during the previous increment. Accordingly, this embodiment includes measuring the temperature at the distal electrode before each incremental withdrawal to check for an adequate temperature for cell coagulation while avoiding an excess temperature that would result in more tissue being coagulated than necessary. Some examples of this embodiment include the probe being withdrawn in incremental withdrawals of a distance that is approximately equal to or less than the length of the probe's active tip. To facilitate withdrawing the probe a specific desired distance, an introducer needle assembly with visible markings may be used whereby a user can visualize how far the introducer has been moved relative to the surface of the patient's skin. In the example of FIG. 8, introducer needle assembly 4 has markings 140 thereupon (for example, on the cannula of the introducer needle assembly). The user may withdraw probe 100 and introducer needle assembly 4 together, by the same distance, while observing the markings 140 to control the distance probe 100 is withdrawn. Typically, introducer needle assembly 4 and probe 100 are coupled together prior to withdrawal. In some embodiments, probe 100 is fittingly seated in introducer needle assembly 4. In some embodiments, the distance between the markings corresponds to (equal or proportional to) the length of active tip 70. For example, a probe with an active tip of 20 mm may be used in conjunction with introducer needle assemblies having distances between the markings of 5 mm, 10 mm or 20 mm. Other examples of this embodiment include the probe being withdrawn in incremental withdrawals slightly less than the length of the probe's active tip.

Figure 7A:
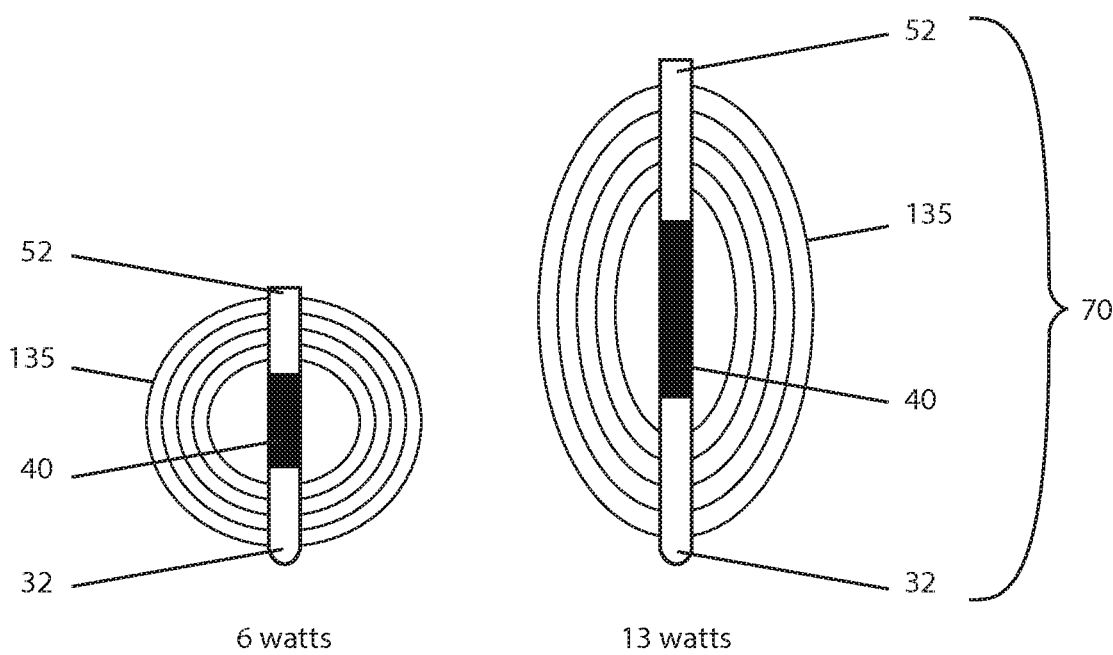
FIGS. 7a and 7b are illustrations of probe distal regions in accordance with embodiments of the present invention, showing temperature distributions as may be achieved using such probes.
Figure 7B:
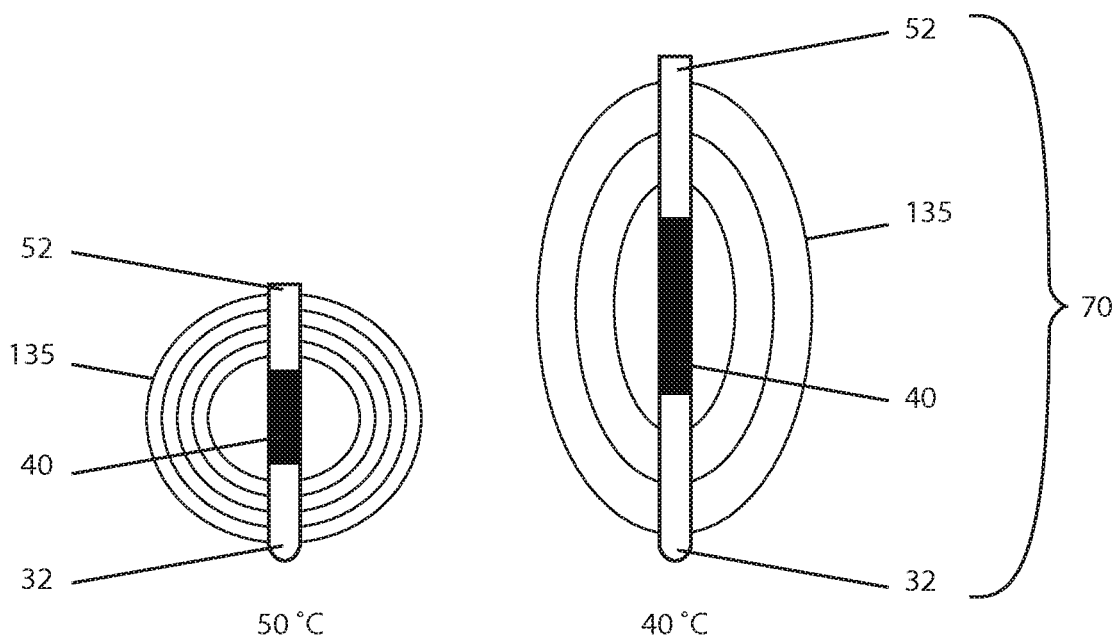

FIGS. 7a and 7b: Probes—Different Sized Active Tips

FIGS. 7a and 7b include exemplary isotherms 135 (temperature distribution), which are proportional or related to electrical flow, to illustrate heating concepts related to probe size. The embodiments of FIGS. 7a and 7b have two electrodes, a proximal electrode 52 with a length $L_1$ (FIG. 1), a distal electrode 32 with a length $L_3$, and an insulator 40 (with a length $L_2$) between the electrodes. In general, a longer active tip 70 requires more power than a shorter active tip to heat tissue to the same temperature because the longer active tip is heating a larger volume of tissue. If the length ratios $L_1$, $L_2$ and $L_3$ of a probe are similar, as shown in the examples of FIG. 7a, then for a given energy (power) output level, the temperature measured at the surface of the probe, typically, is inversely related to the length of the active tip. In the example of FIG. 7a, the shorter active tip is powered at a level of 6 watts and the longer active tip is powered at 13 watts to result in tissue being heated to the same temperature at the distal tip where a temperature sensor is located. Some embodiments may comprise a temperature sensor proximate to distal electrode 32 and/or proximate to the proximal electrode 52, as described hereinabove. Irrespective of the temperature sensor placement, as long as it is consistent, for a given power level, a temperature measured by the temperature sensor at a given position is inversely related to the length of the active tip 70.

Another characteristic of active tips is that, in general, if a shorter active tip is powered at the same level as a longer active tip, it achieves a higher temperature because, with the longer active tip, the heat dissipates into a larger volume of tissue. In the example of FIG. 7b, both active tips are powered at the same level, but the shorter active tip on the left heats tissue, located at the distal tip, to a higher temperature. In FIG. 7b, the longer active tip is shown as having a lower temperature due to the lower power density given the larger surface area.

In general, a procedure for preventing tumor seeding when withdrawing a single energy delivery probe through a path including at least some bone tissue comprises: withdrawing the probe through the path while delivering energy in a bipolar manner from the probe to heat tissue surrounding the path to a temperature sufficient to result in thermal coagulation necrosis of cells.

Furthermore, in alternate embodiments, a procedure for ablating a tumor in tissue and preventing tumor seeding when withdrawing the energy delivery probe can be performed by delivering energy to ablate the target site with a probe cooling system turned on and withdrawing the delivery device incrementally (for example, with the cooling system turned off) through the entry/exit path (the track), while at least partially concurrently (i.e. overlapping in duration) delivering energy to heat tissue surrounding the track to a temperature sufficient to result in thermal coagulation necrosis of cells. In some such procedures the tumor is at least partially in bone tissue. In some alternative embodiments, the procedure is performed by withdrawing the probe substantially continuously. In other alternative embodiments, the procedure is performed without cooling the probe during ablation.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for thermal coagulation necrosis of cells, the method comprising:
   providing a probe having a proximal and, an opposite distal end, an exterior first conductor, an interior second conductor, and exterior first insulator, and an interior second insulator;
   a first portion of the interior second conductor extending through the interior second insulator,
   a first portion of the interior second insulator extending through the exterior first conductor,
   a first portion of the exterior first conductor extending through the exterior first insulator,
   a second portion of the interior second conductor forming an enclosed end portion of the probe, a second portion of the exterior first conductor being spaced from the enclosed end portion of the interior second conductor by a second portion of the interior second insulator;
   withdrawing the probe in increments through tissue via a path that traverses at least some bone tissue;
   for each of the increments, at least partially concurrently delivering energy in a bipolar manner between the enclosed end portion of the second portion of the interior second conductor and the second portion of the exterior first to heat a layer of tissue surrounding the probe to a temperature sufficient for the thermal coagulation necrosis of cells thereby, the energy being supplied to the probe by an electrosurgical generator that is electrically coupled to at least one of the exterior first conductor and the interior second conductor; and
   deactivating a cooling system that extends through the probe and terminates within the enclosed end portion of the interior second conductor when the energy is being delivered to the probe, the probe being not actively cooled by the cooling system during the withdrawal of the probe.

2. The method of claim 1, wherein the path includes a tissue transition zone from one tissue type to another tissue type.

3. The method of claim 1, wherein the energy is radiofrequency electrical energy.

4. The method of claim 1, further comprising coupling the probe to an introducer, wherein the withdrawing of the probe includes withdrawing the probe and the introducer in incremental distances of about a length of the enclosed end portion of the interior second conductor.

5. The method of claim 1, further comprising providing information regarding parameters of the probe to the electrosurgical generator using an interface.

6. The method of claim 1, wherein the electrosurgical generator is configured to automatically detect parameters of the probe.

7. The method of claim 1, further comprising determining a value of an electrical parameter associated with the delivery of the energy to the probe based on the probe being electrically coupled to the electrosurgical generator, the electrical parameter selected from a group including power and voltage.

8. The method of claim 7, wherein the determining of the value of the electrical parameter is performed automatically by the electrosurgical generator.

9. The method of claim 1, further comprising:
   providing the temperature of the layer of tissue surrounding the probe to the electrosurgical generator,
   wherein the delivering of the energy to the probe is based on the temperature of the layer of tissue surrounding the probe.

10. The method of claim 1, further comprising:
    providing an indication to a user when the temperature of the layer of tissue surrounding the probe reaches the temperature sufficient for the thermal coagulation necrosis of the cells,
    wherein the withdrawing of the probe occurs incrementally when the indication is provided.

11. The method of claim 1, further comprising:
    measuring an impedance of at least a portion of the layer of tissue surrounding the probe; and
    terminating the delivering of the energy when the impedance exceeds a threshold.

12. A method for thermal coagulation necrosis of cells, the method comprising:
    providing a probe having a proximal and, an opposite distal end, an exterior first conductor, an interior second conductor, and exterior first insulator, and an interior second insulator;
    a first portion of the interior second conductor extending through the interior second insulator,
    a first portion of the interior second insulator extending through the exterior first conductor,
    a first portion of the exterior first conductor extending through the exterior first insulator,
    a second portion of the interior second conductor forming an enclosed end portion of the probe, a second portion of the exterior first conductor being spaced from the enclosed end portion of the interior second conductor by a second portion of the interior second insulator;

withdrawing the probe through tissue via a path that traverses at least some bone tissue in increments, the increments each having an increment length;

for each incremental withdrawal, delivering energy between the enclosed end portion of the second portion of the interior second conductor and the second portion of the exterior first conductor to heat a layer of tissue surrounding the probe to a temperature sufficient for the thermal coagulation necrosis of cells, the energy being supplied to the probe by an electrosurgical generator that is electrically coupled to the probe;

for each of the increments, measuring a temperature of the layer of tissue surrounding the probe while concurrently heating the layer of tissue surrounding the probe;

automatically detecting at least one probe parameter of the probe; and substantially continuously adjusting an energy delivery parameter of the electrosurgical generator in response to the at least one probe parameter and the temperature of the layer of tissue surrounding the probe, the energy delivery parameter being selected from a group including voltage and impedance.

13. The method of claim 12, wherein the measuring of the temperature of the layer of tissue surrounding the probe being measured by a temperature sensor, the temperature sensor being positioned on an exterior surface of the active end portion of the probe.

14. The method of claim 12, further comprising providing an indication to a user when the temperature of the layer of tissue surrounding the probe reaches the temperature sufficient for the thermal coagulation necrosis of the cells.

15. The method of claim 12, wherein the increment length is less than or equal to a length of the enclosed end portion of the interior second conductor.

16. The method of claim 12, wherein the delivering of the energy includes delivering electrical energy in a bipolar manner.

17. A method for thermal coagulation necrosis of cells, the method comprising:

providing a probe having a proximal and, an opposite distal end, an exterior first conductor, an interior second conductor, and exterior first insulator, and an interior second insulator;

a first portion of the interior second conductor extending through the interior second insulator, a first portion of the interior second insulator extending through the exterior first conductor, a first portion of the exterior first conductor extending through the exterior first insulator, a second portion of the interior second conductor forming an enclosed end portion of the probe, a second portion of the exterior first conductor being spaced from the enclosed end portion of the interior second conductor by a second portion of the interior second insulator;

continuously withdrawing the probe through tissue via a path that traverses at least some bone tissue while concurrently delivering energy between the enclosed end portion of the second portion of the interior second conductor and the second portion of the exterior first conductor to heat a layer of tissue surrounding the probe;

measuring a temperature of the layer of tissue surrounding the probe to confirm thermal coagulation necrosis of cells adjacent to the probe, the measuring of the temperature of the layer of tissue surrounding the probe being measured by a temperature sensor, the temperature sensor being positioned on an exterior surface of the active end portion of the probe;

automatically detecting at least one probe parameter of the probe; and substantially continuously adjusting an energy delivery parameter of the electrosurgical generator or a rate of probe withdrawal based on the at least one probe parameter and the temperature of the layer of tissue surrounding the probe, the energy delivery parameter being selected from a group including voltage and impedance.

18. The method of claim 17, further comprising providing an indication to a user when the temperature of the layer of tissue surrounding the probe reaches the temperature sufficient for the thermal coagulation necrosis of the cells adjacent to the probe.

19. The method of claim 17, wherein the delivering of the energy includes delivering electrical energy in a bipolar manner.

20. The method of claim 17, wherein the probe is withdrawn in increments that are less than or equal to a length of the enclosed end portion of the interior second conductor.

* * * * *